(12) United States Patent
Myllykangas et al.

(10) Patent No.: US 11,517,237 B2
(45) Date of Patent: Dec. 6, 2022

(54) ADAPTER AND EXTERNAL SUPPORT STRUCTURE FOR BIOSIGNAL MEASUREMENT SYSTEM, BIOSIGNAL MEASUREMENT SYSTEM AND CONNECTION METHOD

(71) Applicant: BITTIUM BIOSIGNALS OY, Kuopio (FI)

(72) Inventors: Juha Myllykangas, Kuopio (FI); Arto Remes, Kuopio (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 924 days.

(21) Appl. No.: 16/366,321

(22) Filed: Mar. 27, 2019

(65) Prior Publication Data

US 2020/0305749 A1    Oct. 1, 2020

(51) Int. Cl.
| | | |
|---|---|---|
| *A61B 5/274* | (2021.01) | |
| *H01R 12/71* | (2011.01) | |
| *H01R 13/635* | (2006.01) | |
| *H01R 33/94* | (2006.01) | |
| *H01R 43/26* | (2006.01) | |

(Continued)

(52) U.S. Cl.
CPC .............. *A61B 5/274* (2021.01); *A61B 5/282* (2021.01); *A61B 5/291* (2021.01); *A61B 5/296* (2021.01); *H01R 12/714* (2013.01); *H01R 13/635* (2013.01); *H01R 33/94* (2013.01); *H01R 43/26* (2013.01); *A61B 2562/227* (2013.01);

(Continued)

(58) Field of Classification Search
CPC ......... A61B 5/274; A61B 5/296; A61B 5/291; H01R 12/714; H01R 33/94

USPC ......................................................... 600/393
See application file for complete search history.

(56) References Cited

U.S. PATENT DOCUMENTS 9,700,227 B2 *   7/2017   Bishay ................... A61B 5/259
9,705,239 B2 *   7/2017   Cheng ................ H01R 13/5224
(Continued)

FOREIGN PATENT DOCUMENTS

| EP | 2 468 181 | 6/2012 |
|---|---|---|
| EP | 3 016 586 | 5/2016 |
| WO | 2015/189476 | 12/2015 |

OTHER PUBLICATIONS

Extended European Search Report dated Jul. 2, 2020 in corresponding European Application No. 20159964.4, 3 pages.

*Primary Examiner* — Alexander Gilman
(74) *Attorney, Agent, or Firm* — Nixon & Vanderhye PC (57) ABSTRACT

A biosignal measurement system comprises an adapter for a biosignal measurement device, and an external support structure separate from the adapter. The adapter comprises tool-less connectors, which are repeatedly connectable to and disconnectable from their counter connectors of the external support structure, and a device connector, which has an electrical connection with the tool-less connectors and which has a connection with the biosignal measurement device that the adapter carries. The external support structure comprises an electrode support structure with electrodes and tool-less counter connectors, the electrodes and the tool-less counter connectors having an electrical connection therebetween. The electrodes form an electrical contact with skin for receiving the biosignal. The counter connectors are in electrical contact with the connectors of the adapter for transferring the biosignal to the biosignal measurement device through the adapter.

11 Claims, 7 Drawing Sheets

(51) Int. Cl.
*A61B 5/282* (2021.01)
*A61B 5/291* (2021.01)
*A61B 5/296* (2021.01)
*H01R 13/627* (2006.01)

(52) U.S. Cl.
CPC ........ *H01R 13/627* (2013.01); *H01R 2201/12* (2013.01); *H01R 2201/20* (2013.01)

(56) References Cited

U.S. PATENT DOCUMENTS

| | | | |
|---|---|---|---|
| 9,986,929 B1* | 6/2018 | Dunphy | A61B 5/282 |
| 10,327,657 B2* | 6/2019 | Spencer | A61B 5/259 |
| 10,433,748 B2* | 10/2019 | Bishay | A61B 5/0022 |
| 10,893,818 B2* | 1/2021 | McClung | A61B 5/282 |
| 11,083,371 B1* | 8/2021 | Szabados | A61B 5/6833 |
| 2008/0058623 A1* | 3/2008 | Lee | A61B 5/022 |
| | | | 600/344 |
| 2008/0275322 A1* | 11/2008 | Kim | A61B 5/14552 |
| | | | 600/324 |
| 2010/0191074 A1* | 7/2010 | Chou | G16H 40/67 |
| | | | 600/301 |
| 2010/0331649 A1* | 12/2010 | Chou | A61B 5/0006 |
| | | | 600/595 |
| 2015/0351690 A1* | 12/2015 | Toth | A61B 5/14517 |
| | | | 600/391 |
| 2016/0228060 A1* | 8/2016 | Mazar | A61B 5/282 |
| 2017/0056650 A1* | 3/2017 | Cohen | A61B 5/68335 |
| 2017/0258358 A1* | 9/2017 | Bishay | A61B 5/259 |
| 2018/0249922 A1* | 9/2018 | McClung | A61B 5/259 |

* cited by examiner

ADAPTER AND EXTERNAL SUPPORT STRUCTURE FOR BIOSIGNAL MEASUREMENT SYSTEM, BIOSIGNAL MEASUREMENT SYSTEM AND CONNECTION METHOD

FIELD

The invention relates to an adapter and an external support structure for a biosignal measurement system, the biosignal measurement system and a connection method.

BACKGROUND

An electronic device, which measures biosignals such as ECG (ElectroCardioGram) and EEG (ElectroEncephaloGram), must be well contacted with the electrodes that are in contact with the body and mechanically reliably fixed to its support. The electrodes of the electronic device wear quickly and their contacts with the skin may become unpredictable. Although an electrode structure separate from a data processing part is available, the electrode structure, which has to be replaced often due to the wear, is still complicated and expensive. Hence, there is a need for improvement.

BRIEF DESCRIPTION

The invention is defined by the independent claims. Embodiments are defined in the dependent claims.

LIST OF DRAWINGS

Example embodiments of the present invention are described below, by way of example only, with reference to the accompanying drawings, in which.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned. All combinations of the embodiments are considered possible if their combination does not lead to structural, operational or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Figure 1A:
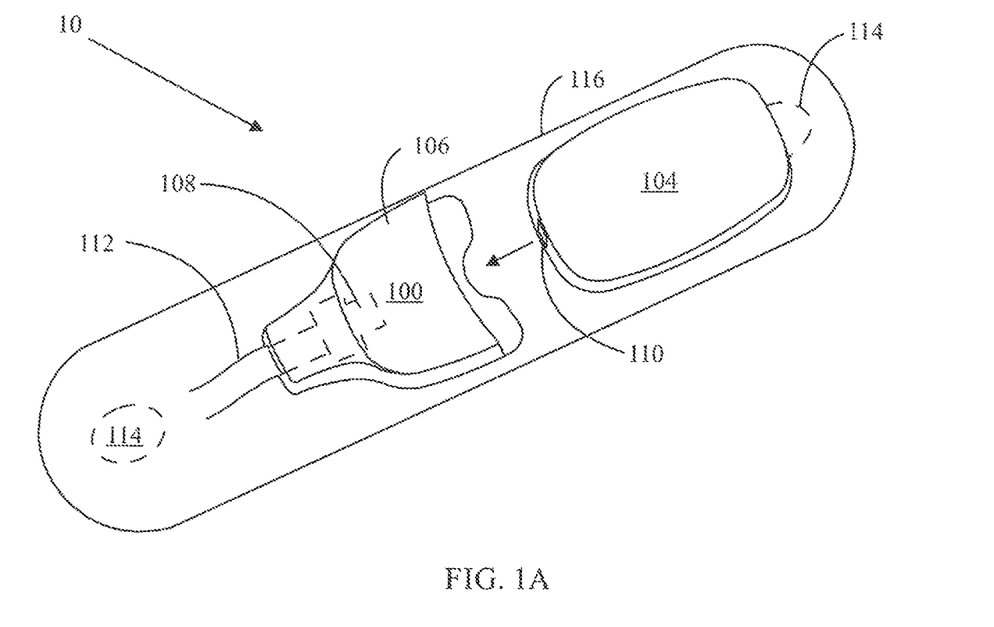
FIGS. 1A and 1B illustrate examples a biosignal measurement system.
Figure 1B:
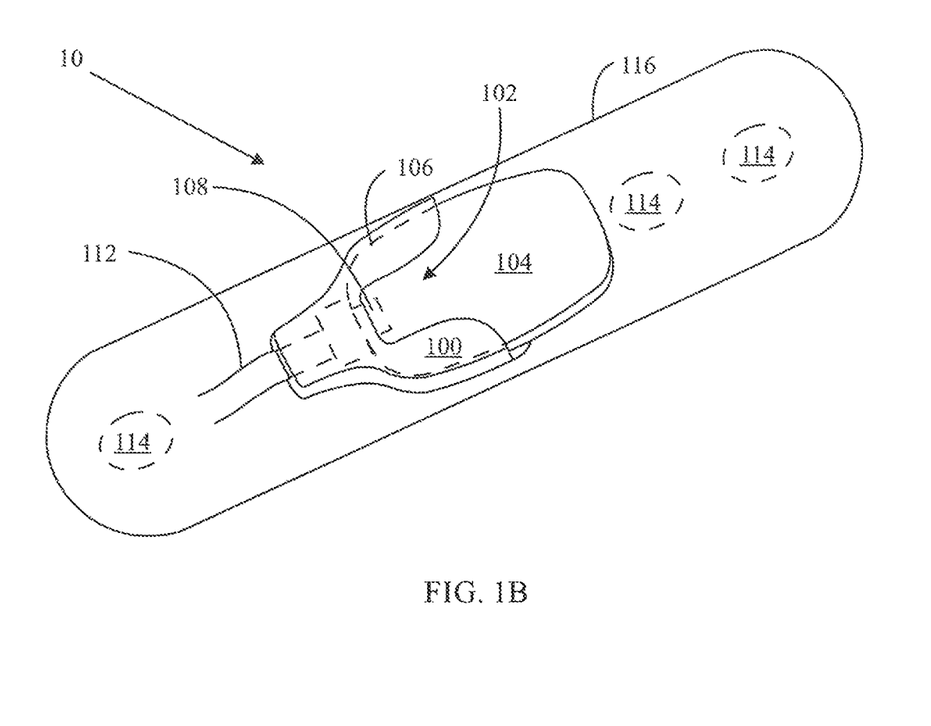

FIGS. 1A and 1B illustrate examples of a biosignal measurement system 10. The holder 100 may be made of polymer such as plastic. The biosignal processing device 104 may be an electronic device, which may convert an analog biosignal it receives to a digital biosignal. The biosignal processing device 104 may also filter the biosignal in an analog or in a digital form. Additionally or alternatively, the biosignal processing device 104 may perform data processing of the biosignal, and it may also store data of the biosignal and/or a result of its processing. The biosignal may be related to heart rate variability, electrocardiogram, electromyogram, electroencephalogram or the like for example.

In FIG. 1A, the biosignal processing device 104 is outside the holder 100. The array in FIG. 1A illustrates the fact that the biosignal processing device 104 may be inserted into the holder 100. In FIG. 1B, the biosignal processing device 104 is at least partly inside the holder 100.

A wall 106 of the holder 100 may form a pocket, and the wall 106 may follow an outer contour of the biosignal processing device 104. The pocket is a free space or volume into which at least a part of the biosignal processing device 104 may fit accurately. A degree of precision with which the surfaces of the biosignal processing device 104 and the wall 106 of the holder 100 are adapted to each other may be high enough to enable operation with one hand or without seeing the actual movement of processing device 104 when inserting the biosignal processing device 104 into or removing the biosignal processing device 104 from the holder 100. A friction between an outer surface of the biosignal processing device 104 and an inner surface of the holder 100 may keep the biosignal processing device 104 in the holder 100 even under accelerations caused by sport activities or in upside down positions. The fit between the biosignal processing device 104 and the holder 100 may be rather tight resulting in a suitable friction and suction force.

Polymer material of the holder 100 may also be slightly flexible and even stretchable which enables to achieve a suitable tightness and friction and suction force between the holder 100 and the biosignal processing device 104. In an example of FIG. 1B, the holder 100 has a slit 102 in the front part whereas the holder 100 of FIG. 1A does not have it. The slit 102 may increase flexibility of the holder 100 but although the slit 102 is optional, it is not necessary. The pocket may have the wall 106 round the biosignal processing device 104 in a continuous hemispherical manner, which is more secure and efficient than a wall that has a shape of a band round the biosignal processing device 104, for example. Still, the hemispherical wall 106 allows easy removal of the biosignal processing device 104 from the pocket.

The holder 100 has a device connector 108 inside the holder 100, and the device connector 108 is connected to a counter connector 110 of the biosignal processing device 104 in FIG. 1B (counter connector 110 is shown in FIG. 1A).

The device connector 108 of the holder 100 is electrically coupled with an adapter wire connection 112, which is connected to electrodes 114 of a system support structure 116. The electrodes 114 may be on an opposite side of the system support structure 116 with respect to the holder 100 and the biosignal processing device 104. The electrodes 114 are configured to be in connection with skin 258 and receive the biosignal from the skin 258 (skin is shown in FIG. 2).

Figure 2:
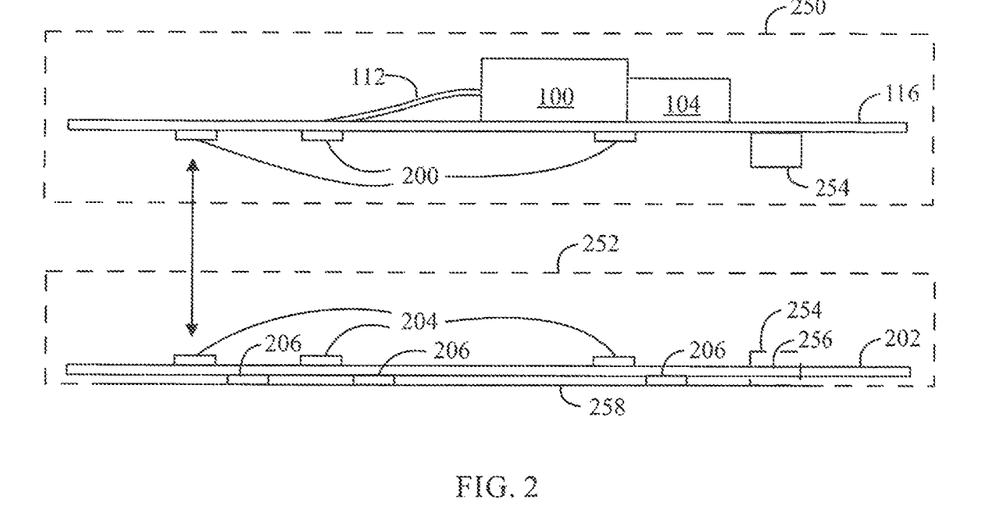
FIG. 2 illustrates an example of a biosignal measurement system, which has a separate external support structure with respect to the system support structure.

FIG. 2 illustrates an example of a new biosignal measurement system 10, which has a separate external support structure 252 with respect to the system support structure 116. The external support structure 252 comprises an electrode support structure 202, a number of tool-less counter connectors 204 and electrodes 206. A number of tool-less connectors 200 of the system support structure 116 corresponds to the number of tool-less counter connectors 204 of the electrode support structure 202. The number of the tool-less connectors 200 is at least two and the number of the tool-less counter connectors 204 is at least two. The tool-less connectors 200 are separate from each other and the tool-less counter connectors 204 are separate from each other.

In an embodiment, the electrodes 206 may have one or more elevations and depressions at the side pressed against the skin 258 in order to have a good contact with the skin 258. The skin contact is similar also in other Figures although it is not drawn in them. Gel may be used between the electrodes 206 and the skin 258 to improve the reception of the biosignal by the electrodes 206 from the skin 258. The conductivity between the tool-less connectors 200 and the tool-less counter connectors 204 may also be improved with a gel or liquid that is electrically conductive.

In an embodiment, the number of the tool-less connectors 200 is three and the number of the tool-less counter connectors 204 is three, for example, without limiting to that.

A constellation of the connectors 200 and a constellation of the counter connectors 204 is the same, and the distances between corresponding connectors 200 and counter connectors 204 are the same such that the locations of the connectors 200 and the locations of the counter connectors 204 are aligned with respect to each other. When the number of the tool-less connectors 200 is at least three, the tool-less connectors 200 may have locations in an asymmetrical manner in the constellation such that a wrong coupling between the tool-less connectors 200 and the tool-less counter connectors 204 is not possible. In the asymmetrical constellation, a distance between two tool-less connectors may be different from a distance between two other tool-less connectors, where at least one tool-less connector is not common to said two tool-less connectors and the two other tool-less connectors (this feature is shown in FIGS. 2 to 5 and 8). The tool-less connectors 200 and the counter connectors 204 may allow a quick connection and disconnection, and thus they may be called quick connectors 200 and quick counter connectors 204. The connection between the connectors 200 and the counter connectors 204 may be galvanic.

Each of the tool-less connector 200 and the tool-less counter connector 204 are made of electrically conductive material. The material may be metal or electrically conductive polymer. Also here, the combination of the holder 100 and the system support structure 116 form an adapter 250 that is revised for the biosignal measurement system 10. The system support structure 116 may comprise the adapter wire connection 112 fully or partly.

The tool-less connectors 200 are repeatedly connectable to and disconnectable from their counter connectors 204. The connection between the tool-less connectors 200 and the counter connectors 204 being electrical and/or galvanic. The counter connectors 204 have an electrical connection with electrodes 206 for reception of a biosignal.

The device connector 108 has an electrical connection with the tool-less connectors 200 and a biosignal measurement device 104. The adapter 250 carries the biosignal device 104 such that the biosignal device 104 is on the system support structure 116 which may surround it fully or partly.

In an embodiment, a height of the connectors 200 may be less than about 3 mm, for example. In an embodiment, a height of the connectors 200 may be less than about 2 mm, for example. In an embodiment, a height of the connectors 200 may be less than about 1 mm, for example. A height of the counter connectors 204 may be about the same as a height suitable for or in an embodiment of the connectors 200. Said height may be measured in a direction parallel to a force used for a connection and a disconnection between a connector 200 and a counter connector 204.

A connector 200 and a counter connector 204 can be connected to and disconnected from each other using a finger force of applied thereto by fingers of a person.

A pair of a connector 200 and a counter connector 204 may be realized as a snap-together-fastener.

Figure 3:
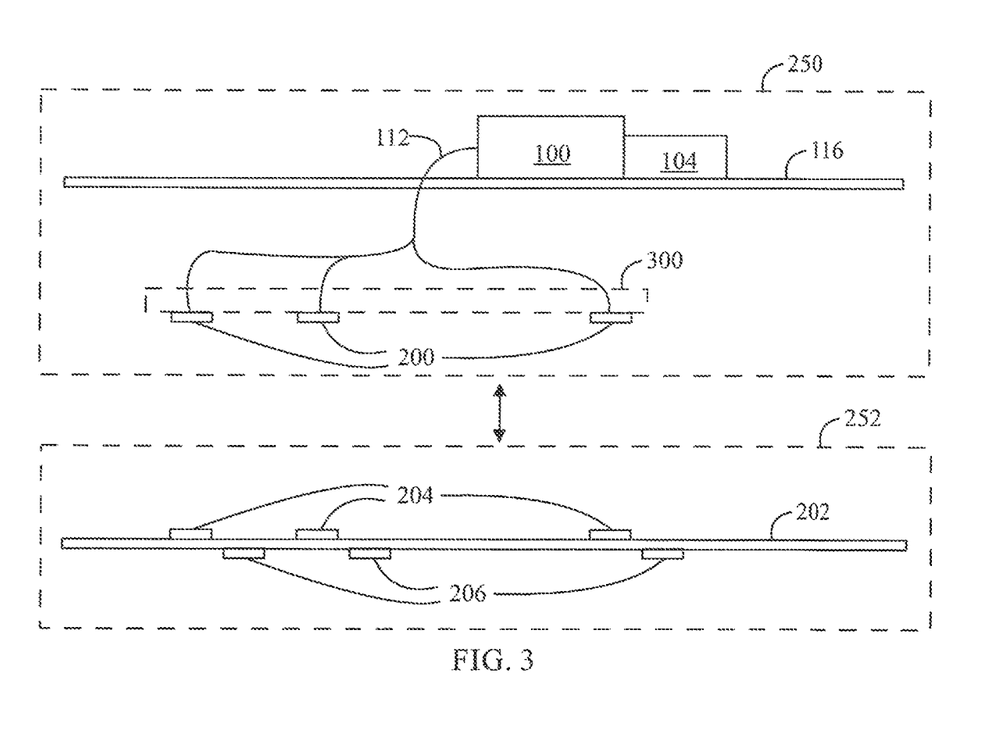
FIG. 3 illustrates an example of an adapter wire connection, which connects electrically the tool-less connectors and the device connector.

FIG. 3 illustrates an example of the biosignal measurement system 10, where the adapter 250 may comprise an adapter wire connection 112, which connects electrically the tool-less connectors 200 and the device connector 108. In this embodiment, the adapter wire connection 112 may extend outside an outer surface of the system support structure 116 such that the tool-less connectors 200 may move freely at a distance from the adapter 250, the distance depending on a length of the adapter wire connection 112. In an embodiment, the tool-less connectors 200 may be attached to or be in fixed positions on or at least partly in a connector support 300. The connector support 300 may be made of polymer and/or a printed circuit board, for example.

In any embodiment, where the adapter wire connection 112 extends outside an outer surface of system support structure 116, the extended part of the adapter wire connection 112 is not a part of the system support structure 116.

Figure 4:
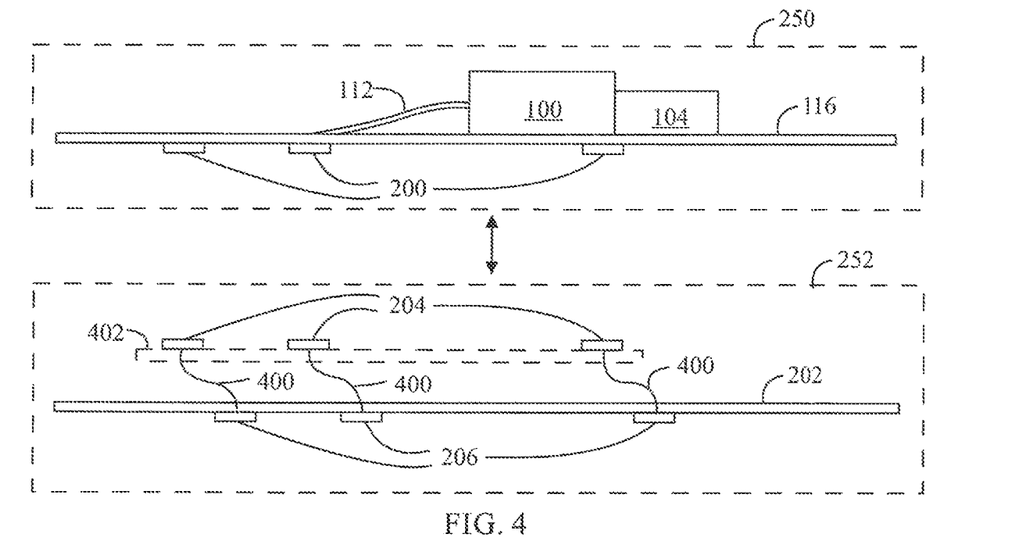
FIG. 4 illustrates an example of an electrode wire connection, which connects the electrically the tool-less counter connectors and the electrodes.

FIG. 4 illustrates an example of the biosignal measurement system 10, where the external support structure 252 may comprise an electrode wire connection 400, which connects the electrically the tool-less counter connectors 204 and the electrodes 206. In this embodiment, the electrode wire connection 400 may extend outside an outer surface of the electrode support structure 202 such that the tool-less counter connectors 204 may move freely at a distance from the electrode support structure 202, the distance depending on a length of the electrode wire connection 400.

In an embodiment, the tool-less counter connectors 204 may be attached to or in fixed positions on or at least partly in a counter connector support 402. The counter connector support 402 may be made of polymer and/or a printed circuit board, for example.

In any embodiment, where the electrode wire connection 400 extends outside an outer surface of electrode support structure 202, the extended part of the adapter wire connection 112 is nota part of the system support structure 116.

Figure 5:
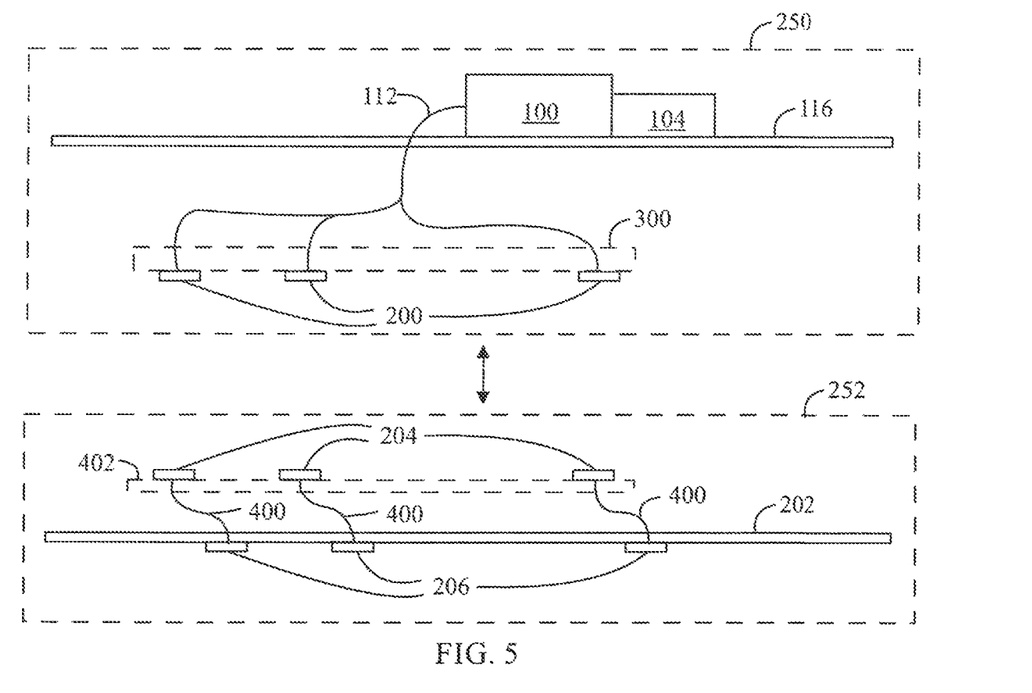
FIG. 5 illustrates an example of the biosignal measurement system, which has the adapter wire connection of FIG. 3 and the electrode wire connection FIG. 4.

FIG. 5 illustrates an example of the biosignal measurement system 10 both the adapter wire connection 112 and the electrode wire connection 400. In this embodiment, the adapter 250 and the external support structure 252 may move freely at a distance from each other, the distance depending on a length of the adapter wire connection 112 and the electrode wire connection 400.

The electrodes 206 are configured to be in connection with skin 258 and receive the biosignal from the skin 258. The biosignal may be generated by a human or animal. The holder 100 and the system support structure 116 combined may form an adapter 250 of the biosignal measurement system 10. However, the adapter 250 does not necessarily have the holder 100.

In FIGS. 2 to 5, the counter connectors 204 are in electrical contact with connectors 200 of the adapter 250 for transferring the biosignal to the biosignal measurement device 104 through the system support structure 116.

Figure 6:
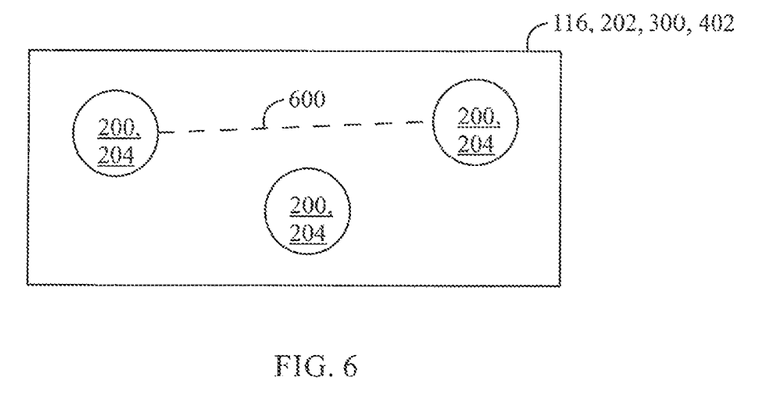
FIG. 6 illustrates an example of an asymmetrical constellation of locations of the tool-less connectors and counter connectors.

FIG. 6 illustrates an example of the asymmetrical constellation of the locations of the tool-less connectors 200 which may be located such that a center point of at least one tool-less connector 200 is outside a line 600 drawn between center points of two tool-less connectors 200.

In an embodiment, which is a more general example of the asymmetrical constellation, at least one point of at least one tool-less connector 200 may be outside a line 600 drawn between center points of two tool-less connectors 200. If a number of tool-less connectors 200 outside the line 600 is even, the tool-less connectors 200 outside the line 600 may be on the opposite side of the line and/or their distances from the line 600 are different. In this example, the two tool-less connectors 200 do not include said at least one tool-less connector. The two tool-less connectors 200 may be freely chosen.

Correspondingly, at least one point of at least one tool-less counter connector 204 may be outside a line 600 drawn between center points of two tool-less counter connectors 200. The constellations of the tool-less counter connectors 204 and the tool-less connectors 200 may have a mirror symmetry.

Figure 7:
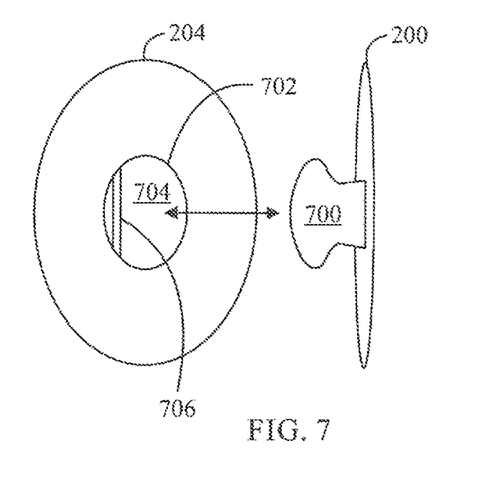
FIG. 7 illustrates an example of a tool-less connector and a corresponding tool-less counter connector.

A tool-less connector 200 and a corresponding tool-less counter connector 204 form a pair of interlocking parts an example of which is shown in FIG. 7. In an embodiment, a connector 200 may have an extension 700 that fits into an aperture 702 of a hole 704 of the counter connector 204. A size of the aperture 702 may be limited by at least one spring 706. When the extension 700 is pushed toward the aperture 702 the at least one spring 706 yields to the force widening the aperture 702, and the extension 700 enters the hole 704 through the aperture 702. Then the at least one spring 706 is in contact with a side of the extension 700 and applies a force against it, which causes a firm attachment between the connector 200 and the counter connector 204 on the basis of friction. Additionally, the extension 700 may be larger at a top that first enters the hole 704 during a connection than a structure of the extensions 700 behind it for increasing the hold.

In an embodiment, a counter connector 204 may have the extension 700 that fits into the aperture 702 of the hole 704 of the connector 200.

In an embodiment, a pair of a connector 200 and a counter connector 204 may comprise a push-grip connector pair.

In an embodiment, a pair of a connector 200 and a counter connector 204 may comprise a push-fit connector pair.

In an embodiment, at least one of the number of the connectors 200 may comprise a snap fastener and at least one of the number of the counter connectors 204 that is a pair of the at least one of the number of the connectors 200 may comprise a counter snap fastener pair. The snap fastener may also be called as a press stud or a popper, for example.

The tool-less connectors 200 may be attached to the system support structure 116 by using a riveter or pliers, for example. Correspondingly, the counter connectors 204 may be attached to the electrode support structure 202 by using a riveter or pliers, for example. The electrode support structure 202 may be made of polymer, for example. The polymer may comprise polyethylene terephthalate (PET), for example. The electrode support structure 202 may be thinner than about 0.5 mm, for example. The system support structure 116 may be made of polymer, for example. The system support structure 116 may, additionally or alternatively, comprise a circuit board, such as a flexible printed circuit board, rigid flexible printed circuit board supported by FR-4 stiffener. The use of FR-4 stiffens the flexible printed circuit board in the area where it is applied, and the stiffer part of FR-4 allows a much denser layout of electrical and potentially other components than the flexible part.

Figure 8:
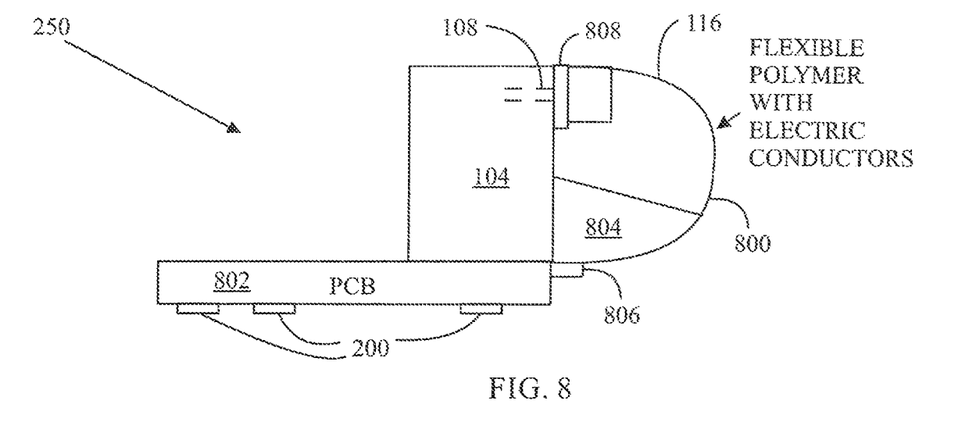
FIG. 8 illustrates an example of the adapter.

FIG. 8 illustrates an example of the adapter 250, which may have a circuit board 802, such as PCB or FR-4 supporting the connectors 200 and the biosignal processing device 104. In this example, there is no separate holder 100. The system support structure 116 may comprise in this example a flexible polymer structure 800 with electric conductors and the circuit board 802. The electric conductors of the flexible polymer structure 800 can be considered the adapter wire connection 112 or its part. The biosignal processing device 104 may be attached to the circuit board 802, and the flexible polymer structure 800 with electric conductors may bend 180° such that the device connector 108 at the opposite end and side can contact with the biosignal processing device 104. The assembled adapter PCB can be soft overmolded into one ready adapter product.

The assembled adapter 250 may be soft overmolded into one ready adapter product.

In an embodiment, a battery 804, which may be charged, may reside within a curved area formed by bending the flexible polymer structure with electric conductors 800. The battery 804 may feed electrical energy to the biosignal processing device 104. In an embodiment, the battery 804 may feed electrical energy to an electrical circuit of the system support structure 116, the electrical circuit being separate but potentially in contact with the biosignal processing device 104 for measurement information transfer. In an embodiment, the battery 804 may feed electrical energy to electrodes 206, if they are electrically active.

In an embodiment, the electrical circuit of the support system 116 may be an autonomous measurement device of at least one biosignal. In that way, the electrical circuit of the system support structure 116 may perform measurements also without the biosignal processing device 104. The electrical circuit of the system support structure 116 may comprise at least one processor, at least one memory and a suitable computer program in a manner shown in FIG. 13 and explained relating to FIG. 13. Then the electrical circuit of the system support structure 116 may process the biosignal received from the human or animal.

In an embodiment, the biosignal measurement system 10 may comprise a radio frequency identification tag 806 for authentication of the adapter 250. In that manner, the biosignal processing device 104 and the adapter 250 which have authorization or are otherwise suitable for each other may be electrically and mechanically coupled together.

In an embodiment, the adapter 250 may comprise an ejector 808 for easy removal of the biosignal processing device 104 from the adapter 250.

Figure 9:
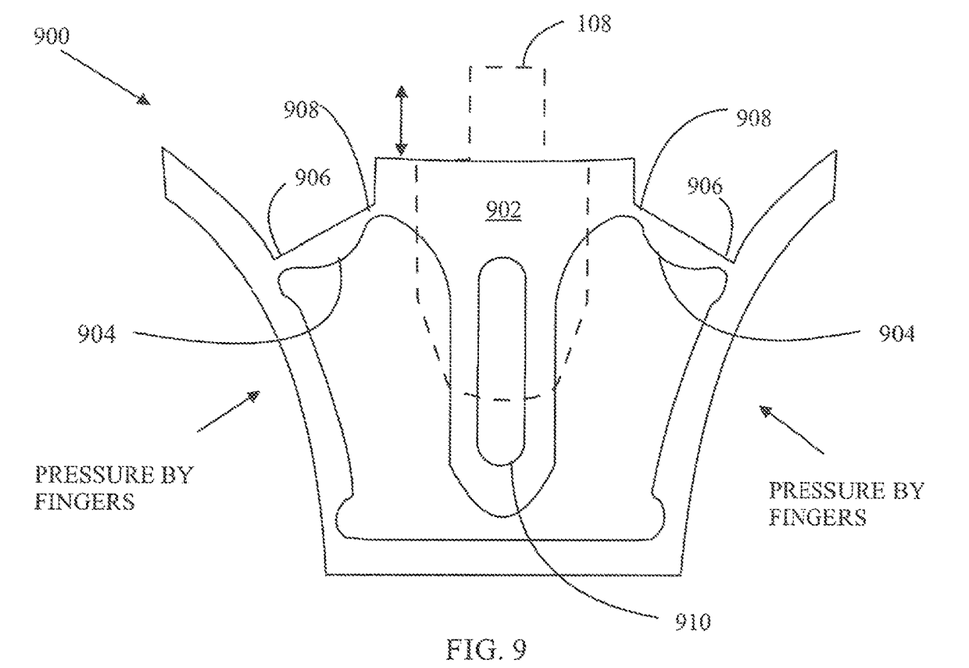
FIG. 9 illustrates an example of a hinged piston associated with the device connector for pushing the biosignal processing device outward from the connection.

In an embodiment an example of which is illustrated in FIG. 9, the ejector 808 may comprise a mechanism 900, which causes a force that helps to remove the biosignal processing device 104 from the adapter 250, i.e. from the holder 100 or the system support structure 116 without the holder 100. The force is a response to pressure against the mechanism 900 adjacent to but behind the connector 108.

The pressure against an outer surface of the mechanism 900 may be caused by a user when he/she presses the mechanism 900 by his/her fingers, for example. The force against and the movement of the biosignal processing device 104 with the help of the force provided by the mechanism 900 makes it easy to detach the biosignal processing device 104 from the coupling. The biosignal processing device 104 may be gripped with fingers from the upper part for lifting the biosignal processing device 104 and additionally the pressure against the mechanism 900 results in a convenient removal of the biosignal processing device 104. In an embodiment, the mechanism 900 may move about 1 mm when a pressure is applied. In an embodiment, the mechanism 900 may be configured to move about 2 mm when a pressure is applied. The biosignal processing device 104 may be configured to move about the same length as the mechanism 900 when a pressure is applied at the rear section 114. Hence, it is possible to insert the biosignal processing device 104 into the holder 100 and remove the biosignal processing device 104 from the holder 100 even with a single hand.

In an embodiment an example of which is shown in FIG. 9, the mechanism 900 may comprise a piston 902 that actually may move back and forth. The mechanism 900 may also comprise least one lever 904 hinged to the piston 902. A hinge 906 between the lever 904 may be made of polymer. The hinge 908 between the lever 904 and the piston 902 may be made of polymer. A common molding process enables this kind of hinging.

In an embodiment, the at least one lever 904 may be pushed forward and turn between the hinges 906, 908 in response to the pressure. The lever 904 may turn between the hinges 906, 908. Then the lever 904 may move the piston 902 forward in response to the pressure. The piston 902 may then move the biosignal processing device 104 along the device connector 108, which is immobile, loosening the connection.

In an embodiment, the piston 902 may have a slit 910 into which a fixed rail may be matched for guiding the movement of the piston 902 in its movement back and forth.

Figure 10:
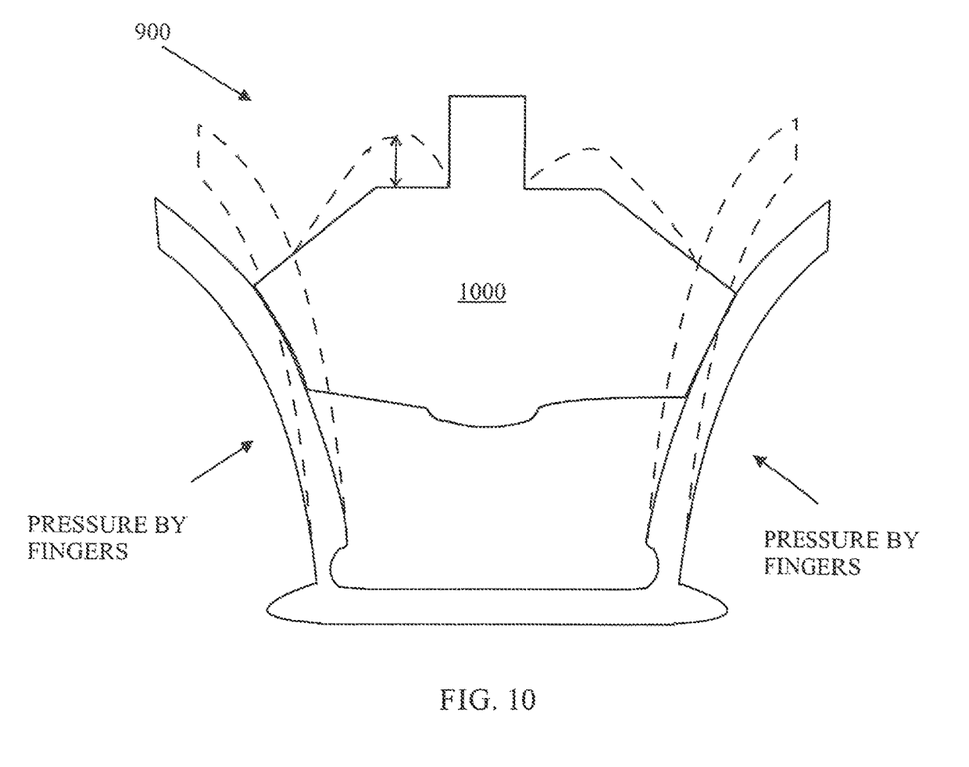
FIG. 10 illustrates an example of elastic material associated with the device connector for pushing the biosignal processing device outward from the connection.

In an embodiment an example of which is shown in FIG. 10, the adapter 250 may comprise elastic material 1000. The pressure against the mechanism 900 may cause the elastic material 1000 to reshape, push against and move the biosignal processing device 104 outwards from its coupling for enabling an easy removal. The dashed lines show the movement of the mechanism 900 and the movement of elastic material 1000. The elastic material 1000 may revert to its original shape after the pressure ceases.

Figure 11A:
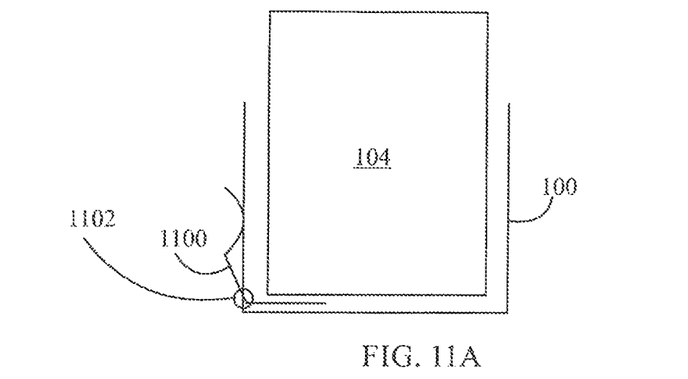
FIGS. 11A and 11B illustrate an example of a lever for pushing the biosignal processing device outward from the polymer holder.
Figure 11B:
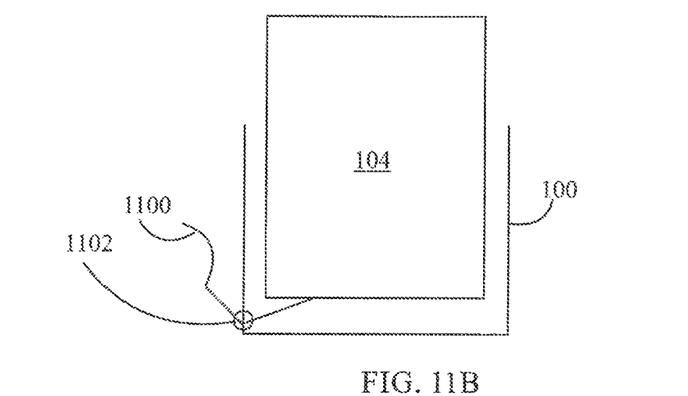

In an embodiment an example of which is shown in FIGS. 11A and 11B, the mechanism 900 may comprise a hand lifted lever 1100 outside the holder 100. The lever 1100 may be hinged (hinge 1002) at the wall of the holder 100. Then when the lever 1100 is turned, an angled part of the lever 1100 inside the holder 100 is lifted upwards whereby pushing also the biosignal processing device 104 out of the holder 100 and loosening the electrical connection.

Figure 12:
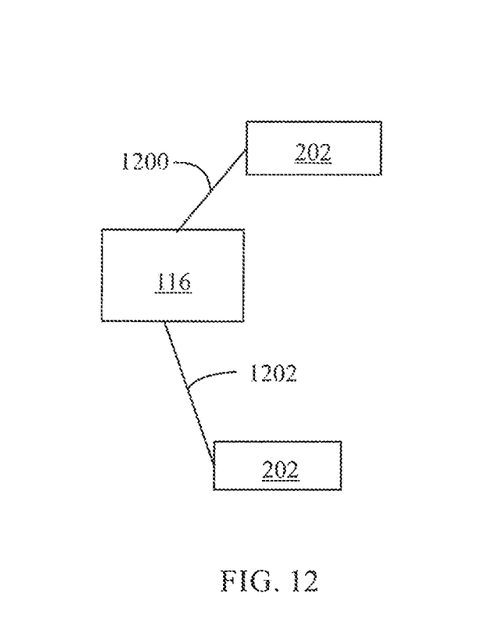
FIG. 12 illustrates an example where the system support structure has wired connections to a plurality of electrode support structures.

FIG. 12 illustrates an example of an embodiment, where the system support structure 116 may have wired connections 1200, 1202 to a plurality of electrode support structures 202. The wired connections 1200, 1202 may be realized as shown in FIG. 3, 4 or 5. Hence, the wired connections 1200, 1202 may be based on the adapter wire connection(s) 112 and/or the electrode wire connection(s) 400.

Figure 13:
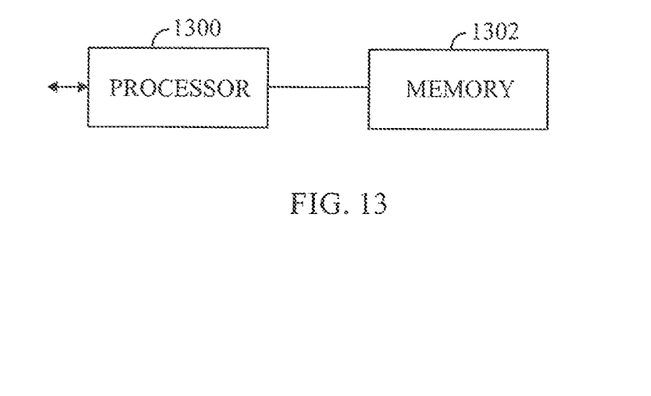
FIG. 13 illustrates an example where the biosignal processing device has at least one processor and at least one memory.

In an embodiment an example of which is shown in FIG. 13, the biosignal processing device 104 may comprise one or more processors 1300, and one or more memories 1302 that may include a computer program code. The one or more memories 1302 and the computer program code may, with the one or more processors 1300, cause the biosignal processing device 104 at least to process the biosignal received from the human or animal.

The electrode support structure 202 may have a PET-layer with AgCl-printed electrodes. The system support structure 116 may be made with one rigid-flex PCB such that the biosignal processing device 104 overmold with polymer.

The electrode support structure 202, which may be disposable, may be made as simple as possible. Another aspect of this invention is to enable active circuitry outside the system support structure 116 housing to accommodate size-consuming electronics such defibrillation protection circuitry. This protection circuitry enables the system support structure 116 to be used in larger business area (such as hospital ISO 60601-1-27 requirements). Any active electronics cannot be on the disposable electrode support structure 202 due to price constraint.

A cheap disposable electrode support structure 202 may be achieved by using industry standard snap-connectors on disposable part to connect the tool-less connectors. A costly USB connector is not needed on the electrode support structure 202 and there is no need for connector assembly on reflow, overmolding etc.

This invention may overcome multiple problems. The electrode support structure 202 may be made disposable electrodes. The electrode support structure 202 may also be cheaper because it can be made simpler than the one integrated with the adapter 250. The electrode support structure 202 enables multi-channel electrodes through the tool-less connection with a reasonable cost. The electrode support structure 202 enables ISO 60601-1-27—compliant protection circuitry. The electrode support structure 202 enables active electronics to be placed on the adapter 250 without adding any size to the system support structure 116. The electrode support structure 202 enables cost-effective new measurements on disposable patch measurements.

In an embodiment an example of which is illustrated in FIG. 2, the adapter 250 may have at least one part 254 that is connected to the skin 258 via an opening 256 of the electrode support structure 202. The external support structure 252 comprises one or more openings 256 into which the at least one part 254 is insertable for a contact with skin 258. In FIG. 2, the at least one part 254 is drawn with dashed line in the opening 256 which represents a situation in which the tool-less connectors 200 and the tool-less counter connectors 202 are coupled to each other.

The at least one part 254 may comprise sensor(s) of one or more of a plurality of the biosignal types, noise reduction contacts and/or ground contacts, for example. In an embodiment, the one or more biosignal types may include non-ECG biosignals. In an embodiment, the part 254 of the adapter 250 may have a temperature sensor and/or an oxygen saturation sensor, for example. If there are wires 112, 400 between the adapter 250 and the electrode support structure 202, no opening 256 is not necessarily needed because the at least one part 254 may be connected to the skin at a location beside the electrode support structure 202. Then, the tool-less connectors 200 may be electrically insulted from a contact with the skin. For the electrical insulation, the tool-less connectors 200 may be covered by a dielectric material, which insulates electrically. The dielectric material may comprise plastic, resin and/or varnish, for example.

In an embodiment, the battery 804 (see FIG. 8) may feed electrical energy to the at least one part 254. In an embodiment, the battery 804 (see FIG. 8) may feed electrical energy to the temperature sensor and/or the oxygen saturation sensor.

The electrode support structure 202 enables nickel- and copper free electrodes. The electrode support structure 202 enables electrodes to be absolutely passive and follow an electrocardiogram-electrode standard without any problems. The electrode support structure 202 may be used to measure electroencephalography (EEG) and electromyography (EMG). The electrode support structure 202 enables IPR protection circuits to be used against illegal copying and information theft.

Figure 14:
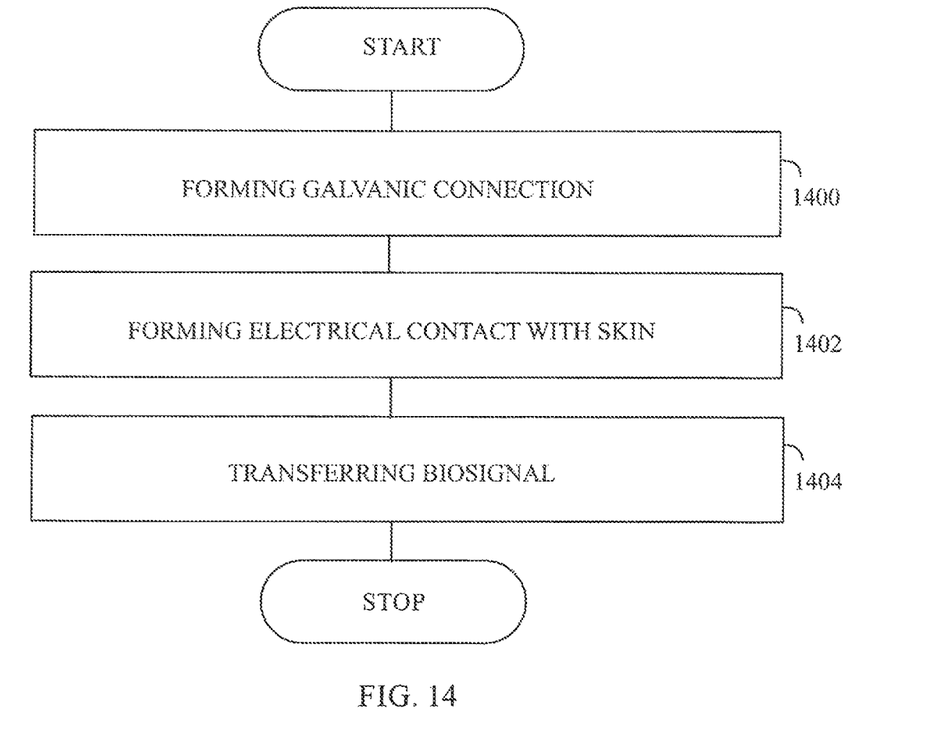
FIG. 14 illustrates of an example of a flow chart of a connection method.

FIG. 14 is a flow chart of the measurement method. In step 1400, a galvanic connection, which is repeatedly disconnectable, is formed between tool-less connectors 200 of an adapter 250 and counter connectors 204 of an external support structure 252, which is separate from the adapter 250, a device connector 108 of the adapter 250 having an electric connection with the tool-less connectors 200 and the biosignal measurement device 104 that the adapter 250 is configured to carry. In step 1402, using electrodes 206 of the external support structure 252 an electrical contact is formed, with skin for receiving the biosignal, the electrodes 206 and the tool-less counter connectors 204 having an electrical connection therebetween. In step 1404, the biosignal is transferred to the biosignal measurement device 104 while the connectors 200 are in electrical contact with the counter connectors 204.

It will be obvious to a person skilled in the art that, as technology advances, the inventive concept can be implemented in various ways. The invention and its embodiments are not limited to the example embodiments described above but may vary within the scope of the claims.

The invention claimed is:

1. An adapter for a biosignal measurement system, wherein the adapter comprises
   tool-less connectors, which are repeatedly connectable to and disconnectable from their counter connectors of an external support structure that also comprises an electrode support structure and electrodes, the counter connectors being configured to have an electrical connection with the electrodes of the external support structure for reception of a biosignal; and
   a device connector, which has an electrical connection with the tool-less connectors and which is configured to have a connection with a biosignal measurement device that the adapter is configured to carry.

2. The adapter of claim 1, wherein the connectors and the counter connectors are connectable to and disconnectable from each other using a finger force.

3. The adapter of claim 1, wherein a pair of one of the connectors and one of the counter connectors is realized as a snap-together fastener.

4. The adapter of claim 1, wherein the adapter comprises a system support structure configured to carry the biosignal measurement device, which includes an adapter wire connection configured to connect electrically the tool-less connectors and the device connector, the adapter wire connection extending outside the system support structure.

5. An external support structure for a biosignal measurement system, wherein the external support structure comprises an electrode support structure with electrodes and tool-less counter connectors, the electrodes and the tool-less counter connectors having an electrical connection therebetween;
   wherein the electrodes are configured to form an electrical contact with skin for receiving a biosignal; and
   wherein the tool-less counter connectors are configured to be in electrical contact with tool-less connectors of an adapter for transferring the biosignal to a biosignal measurement device through the adapter.

6. The external support structure of claim 5, wherein the external support structure comprises an electrode wire connection, which is configured to connect electrically the tool-less counter connectors and the electrodes and which is configured to extend outside an outer surface of the electrode support structure.

7. A biosignal measurement system, wherein the biosignal measurement system comprises an adapter for a biosignal measurement device, and an external support structure separate from the adapter;
   the adapter comprises tool-less connectors, which are repeatedly connectable to and disconnectable from their counter connectors of the external support structure, and a device connector, which has an electrical connection with the tool-less connectors and which is configured to have a connection with the biosignal measurement device that the adapter is configured to carry; and
   the external support structure comprises an electrode support structure with electrodes and tool-less counter connectors, the electrodes and the tool-less counter connectors having an electrical connection therebetween;
   the electrodes are configured to form an electrical contact with skin for receiving a biosignal; and
   the counter connectors are configured to be in electrical contact with the connectors of the adapter for transferring the biosignal to the biosignal measurement device through the adapter.

8. The biosignal measurement system of claim 7, wherein the adapter comprises at least one part, which comprises at least one of the following: sensor(s) of one or more of a plurality of non-ECG biosignal types, noise reduction contacts and ground contacts.

9. The biosignal measurement system of claim 7, wherein the at least one part of the adapter has a temperature sensor and/or an oxygen saturation sensor.

10. The biosignal measurement system of claim 7, wherein the external support structure comprises one or more openings into which the at least one part is insertable for a contact with skin.

11. A connection method, the method comprising forming a galvanic connection, which is repeatedly disconnectable, between tool-less connectors of an adapter and counter connectors of an external support structure including an electrode support structure, which is separate from the adapter, a device connector of the adapter having an electric connection with the tool-less connectors and the biosignal measurement device that the adapter is configured to carry; and forming, using electrodes of the external support structure, an electrical contact with skin for receiving the biosignal, the electrodes and the tool-less counter connectors having an electrical connection therebetween; and transferring the biosignal to the biosignal measurement device while the connectors are in electrical contact with the counter connectors.

\* \* \* \* \*